(12) United States Patent
Stauch (10) Patent No.: US 9,138,266 B2
(45) Date of Patent: Sep. 22, 2015

(54) INTRAMEDULLARY NAIL (75) Inventor: Roman Stauch, Assamstadt (DE)

(73) Assignee: Wittenstein AG, Igersheim (DE)

( * ) Notice: Subject to any disclaimer, the term of this patent is extended or adjusted under 35 U.S.C. 154(b) by 364 days.

(21) Appl. No.: 13/613,932

(22) Filed: Sep. 13, 2012

(65) Prior Publication Data
US 2013/0072932 A1 Mar. 21, 2013

(30) Foreign Application Priority Data

Sep. 15, 2011 (DE) .......................... 10 2011 053 638

(51) Int. Cl.
*A61B 17/72* (2006.01)
*A61B 17/00* (2006.01)

(52) U.S. Cl.
CPC ......... *A61B 17/7216* (2013.01); *A61B 17/7241* (2013.01); *A61B 2017/00991* (2013.01)

(58) Field of Classification Search
USPC .................... 606/62–68, 282, 320, 105, 86 R
See application file for complete search history.

(56) References Cited

U.S. PATENT DOCUMENTS

| 5,976,138 | A | 11/1999 | Baumgart et al. |
| 8,252,063 | B2 | 8/2012 | Stauch |
| 2006/0293683 | A1 | 12/2006 | Stauch |
| 2009/0062798 | A1* | 3/2009 | Conway .......................... 606/63 |
| 2010/0049204 | A1* | 2/2010 | Soubeiran ....................... 606/90 |
| 2011/0060336 | A1* | 3/2011 | Pool et al. ....................... 606/57 |
| 2012/0179215 | A1 | 7/2012 | Soubeiran |

FOREIGN PATENT DOCUMENTS

| DE | 19527822 C1 | 12/1996 |
| DE | 19708279 C2 | 10/1999 |
| DE | 10317776 A1 | 11/2004 |
| DE | 102009011661 A1 | 9/2010 |
| FR | 2949662 A1 | 3/2011 |

OTHER PUBLICATIONS

European Search Report for EP 12184025, dated Nov. 19, 2012.

* cited by examiner

*Primary Examiner* — Pedro Philogene
*Assistant Examiner* — Lynnsy Summitt
(74) *Attorney, Agent, or Firm* — Bachman & LaPointe, P.C.

(57) ABSTRACT

Intramedullary nail for distraction of a long bone with an at least partially hollow shank extending in an axial direction of the intramedullary nail, locking element for locking the shank in a first bone fragment of the long bone, a first inner section which is arranged in axially movable manner within the shank and has a through hole orientated in the radial direction for accommodating a segment bolt for fixing a bone segment of the long bone, wherein the shank has an elongated hole in the area of the inner section for passing through of the segment bolt, an actuator for axially moving the first inner section, wherein a second inner section is arranged within the shank so as to be axially movable.

13 Claims, 4 Drawing Sheets

INTRAMEDULLARY NAIL

BACKGROUND OF THE INVENTION

The invention relates to an intramedullary nail for distraction of a long bone and a modular system.

Intramedullary nails that enable distraction of long bones are known from the prior art. Two bone fragments, a distal fragment and a proximal fragment are displaced relative to one other by means of an intramedullary nail. It is intended for new bone to grow at the point of contact between the two bone fragments. This is achieved by selecting a rate of advance of the intramedullary nail that is sufficiently slow to allow distraction to take place.

It is also known from the prior art to use intramedullary nails that are capable of effecting segment transport, for example the prior art in DE 197 08 279 C2 may be cited here. Such segment transport enables the treatment of large bone defects, of more than 3 cm for example, such as can occur as a consequence of disease or through the effect of force. Large bone defects can also occur in surgical procedures necessitated by bone tumours, and these may also be treated with an intramedullary nail with segment transport depending on the severity of the disease.

A fundamental challenge in the case of intramedullary nails with segment transport is the fixing of the ends of the intramedullary nail in the proximal bone fragment and in the distal bone fragment. Another challenge is stabilisation against rotation.

Thus, DE 197 08 279 C2 suggests a guide sleeve that is fixed in the bone fragment with a screw screwed in in the axial direction of the long bone. As an additional component, the guide sleeve makes the fitting of the intramedullary nail in the bone complicated. The guide sleeve also requires additional clearance in the bone fragment so that the diameter of the opening that has to be created in the bone is large. Furthermore, due to its design the intramedullary nail of the prior art cited above cannot be used for lower leg bones.

The object of the invention is to describe an intramedullary nail or a modular system for an intramedullary nail that improves the systems or intramedullary nails known from the prior art, in particular the drawbacks of the prior art are to be alleviated or eliminated. Desirable are intramedullary nails that require as little surgical effort as possible or enable reliable fixation in the bone fragments. A modular system should be able to be flexibly adapted to different circumstances, for example different bones or different applications such as segment transport or distraction.

SUMMARY OF THE INVENTION

This object is achieved with an intramedullary nail for distraction of a long bone comprising an at least partially hollow shank extending in an axial direction of the intramedullary nail; locking means for locking the shank in a first bone fragment of the long bone; a first inner section of the intramedullary nail is arranged within the shank and is movable in the axial direction and comprises a fixing means for affixing a bone segment of the long bone, wherein the shank has at least one elongated hole in the area of the inner section to enable passing through of the fixing means; an actuator for axially moving the first inner section; and a second inner section of the intramedullary nail arranged movably in an axial direction within the shank and a modular system for the intramedullary nail.

Examples of intramedullary nails have a hollow shank extending in the axial direction of the intramedullary nail. This shank preferably has axially orientated elongated holes for the passing through of segment fixing screws. The arrangement of elongated holes makes it possible to fix a bone segment with a segment fixing screw. The bone segment is usually a part of the bone located between a first bone fragment and a second bone fragment. In certain embodiments the first bone fragment may be a proximal bone fragment or a distal bone fragment. Accordingly the second bone fragment is then a distal bone fragment or in the other case a proximal bone fragment. Exemplary intramedullary nails are particularly suitable for the treatment of fractures or other damage to long bones, and other damage may be for example bone loss due to tumours or through the effect of force. Bones that can be treated with typical intramedullary nails are the upper leg bone (femur) and shin bone (tibia), but the upper arm bone (humerus), the ell (ulna), the radius and that fibula may also be treated. Typical intramedullary nails described here are also particularly suitable for short or young patients, as the structure of exemplary intramedullary nails according to the invention requires a comparatively short bone fragment length for locking.

Typical intramedullary nails in accordance with the invention have a locking means for locking the shank in the first bone fragment of the long bone. In this way the shank may be implanted in a first bone fragment of the long bone fixedly in all directions and all directions of rotation. The shank is thus fixed to the bone fragment in all degrees of freedom. Bolts or screws that penetrate through the shank in the radial direction may particularly be used as locking means. The screws or bolts enable the shank to be anchored in the bone fragment.

Typically, the intramedullary nail comprises an actuator for axial displacement of a first inner section. The first inner section is arranged within the shank so as to be movable in the axial direction. Typical embodiments of the inner section are at least essentially cylindrical. The inner section is preferably formless, that is to say it has, for example, no journals projecting radially outwards, or it only has openings. The inner section preferably has an internal thread which extends over at least part of the inner mantle surface close to the opening to accommodate the actuator spindle. The shank is typically also cylindrical. Usual shank dimensions exhibit a shank diameter that does not exceed 13 mm and remains unchanged over its entire length or at least essentially over its entire length. Other typical intramedullary nails in accordance with the invention have shank diameters not exceeding 12 mm or not exceeding 11 mm. A small diameter offers advantages as this facilitates the insertion of the intramedullary nail and it is only necessary to drill out the medullary space to a small degree.

Preferred first inner sections of the intramedullary nail have at least one radial through hole for accommodating a segment bolt for fixing a bone segment of the long bone. As the segment fixing bolt may also be passed through two opposite, axially aligned elongated holes of the shank, the inner section is simultaneously blocked relative to the shank in terms of the degree of rotational freedom about the longitudinal axis. This also provides the advantage that the bone segment also does not turn about the longitudinal axis of the intramedullary nail during treatment.

Further embodiments comprise a lock for fixing the bone segment. Such a lock offers the advantage of simple design. The lock is preferably arranged perpendicularly to the direction of an actuator shaft. The lock thus preferably forms the first inner section and also the fixing means in one piece. Exemplary embodiments with a multiple-component lock comprise an inner section, typically similar to a nut, and a radially projecting locking element. For this, the lock is typically provided with a recess. This recess preferably engages in positive locking manner in an inner section seated on the spindle, which is designed as a threaded element with a centrally arranged inner thread. This embodiment makes it possible to reduce the structural length or to achieve larger distraction distances.

The actuator is typically accommodated in fixed manner in the shank in such manner that the intramedullary nail may be inserted into the long bone with the actuator mounted. In typical embodiments the intramedullary nail is designed so that the intramedullary nail can be inserted into the long bone with the actuator already mounted, i.e. with the actuator accommodated in the shank. Preferred intramedullary nails allow a procedure with prior incorporation of the actuator (before insertion into the bone) in operations, wherein fragment fixing bolts or other locking means may be anchored in the bone and in the intramedullary nail even with the actuator already in place. In other embodiments the actuator may also be inserted into the intramedullary nail subsequently during an operation. In embodiments, particularly those with a subsequently insertable actuator, means of securing against rotation are typically provided.

Typical intramedullary nails comprise a second inner section, which is arranged in axially movable manner inside the shank. By providing a first and second inner section, it is possible to achieve segment displacement and even distraction of the entire bone, that is to say movement of the two bone fragments relative to one other. Particularly, in such embodiments, the end of the shank that is in the region of the second inner section is movable in the corresponding bone fragment after it has been inserted into a bone. The bone fragment is typically held by means of fragment fixing means or fragment fixing bolts of the second inner section.

The inner sections are normally arranged axially one behind the other in the shank. In embodiments, the inner sections are immediately adjacent or may even be in contact with each other. This offers the advantage that direct force transmission from inner section to inner section for distraction is possible after a segment transport. Contact between the inner sections is not provided in other embodiments. This offers the advantage that, when the bone segment comes into contact with one of the bone fragments at the end of a segment transport, high pressure may be exerted between the segment and the bone fragment, allowing the bone segment to grow together with the bone fragment, even during a distraction following the segment transport. In this context, an advancing force is transmitted from the first inner section with the bone segment to the bone fragment and the second inner section connected thereto, so that the second inner section is pushed back into the shank.

Normally segment transport is performed by slowly moving the bone segment from a bone fragment towards the other bone fragment, during which new bone grows in the resulting gap between the initial bone fragment and the bone segment. A more detailed account can be found in patent specification DE 197 08 279 C2.

The two inner sections are preferably arranged axially one behind the other in the shank without a fixed connection. The inner sections are usually only movable in the axial direction. In typical intramedullary nails the inner sections are axially guided. In typical embodiments the second inner section can be moved independently of the first inner section.

The shank preferably has further elongated holes in the area of the second inner section for enabling pass-through of at least one fragment fixing bolt for fixing a second bone fragment of the bone. Typically, two elongated holes aligned in the axial direction of the shank are provided opposite one another in the shank for enabling pass-through of the one or more fragment fixing bolts. In this context, "in the area of the second inner section" means, for example, an area in which through holes of the second inner section are positioned when the second section is moved as envisaged during use.

The second inner section usually has a radially aligned through hole to accommodate the fragment fixing bolt. In typical embodiments the inner section has two or more radially aligned through holes for accommodating fragment fixing bolts. This has the advantage that the second bone fragment can be securely locked.

Typical intramedullary nails have an actuator-less second inner section. In this context, "actuator-less" means that the second inner section does not have a separate actuator or is not connected to the actuator, for example by means of a shaft grip or push rod. In embodiments, the first inner section is permanently attached to an actuator, whereas the second inner section is freely movable. The displacement path of the second inner section is preferably limited by a limit stop or by the first inner section. During use in embodiments, the second inner section is not moved until the bone segment impacts the second bone fragment or the first inner section directly contacts the second inner section.

A Herzog bend is preferably provided at one end of the shank. This provides the possibility of also using the intramedullary nail in a lower leg bone (tibia). The Herzog bend is preferably provided at the end of the actuator. In typical embodiments the actuator is arranged opposite the second inner section, meaning that the first inner section lies between the second inner section and the actuator. Preferably, with the exception of the Herzog bend and the through holes for bolts or locking means to pass through, the shank is ideally cylindrical. In this context, "ideally cylindrical" means that no other pins or lugs or slots are provided on the shank. In typical embodiments the intramedullary nail is designed in such a way that the Herzog bend and the actuator are arranged proximally. Typically, the actuator is arranged distally to, that is to say behind or below the Herzog bend.

An electric motor with a gear mechanism and a spindle is preferably provided as the actuator. The gear mechanism is preferably a planetary gear as this enables high transmission ratios. For the power supply and control of the actuator a control unit is typically provided that may be wirelessly supplied with energy or control signals via an antenna from outside the body in which the intramedullary nail is being used. In embodiments the control unit is able to wirelessly transmit or send captured parameters such as, for example the force required for displacement or an already travelled displacement path. In other embodiments a shape-memory alloy or another form of drive unit is envisaged as the actuator.

Typically, the first inner section and the second inner section are cylindrical in shape. In conventional embodiments the diameters of the first and second inner sections are identical. In preferred embodiments the inner sections have no contour variations, that is to say the inner sections are contourless. This has the advantage of simple manufacturing and guaranteed avoidance of tilting or similar. However, it is also possible to provide lugs that serve in addition to the fixing bolts to define the position of the inner sections within the shank. The term "contourless" relates to the external defining surface of each inner section, particularly the first inner section usually has an internal thread. The first inner section is preferably designed as a sleeve, which has an internal thread for engaging with the spindle. The second inner section is preferably designed as a cylinder. The first inner section is linearly driven by the spindle element and the connected actuator, which is positioned in the actuator shank.

A further aspect relates to a modular system for intramedullary nails, particularly for intramedullary nails for distraction of a long bone. The modular system comprises a locking shank with a locking means for locking the locking shank in a first bone fragment of the long bone, an axially extending hollow shank section in which a first inner section is arranged so as to be movable in the axial direction and which has a radially aligned through hole for accommodating a bolt. The bolt is typically a fixing bolt, particularly a segment fixing bolt or a fragment fixing bolt for fixing a bone segment or a second bone fragment. The modular system also typically comprises an actuator shank which has an actuator arranged in the actuator shank for axially displacing a first inner section. The locking shank, the actuator shank and the shank section may be connected to each other in this order to form an intramedullary nail. Particularly welding is used as the connection method, though it is also possible to envisage screw-type connections or other connections. Welded connections have the advantage that they are space-saving. The locking shank, the drive shank and the shank section preferably have identical diameters or a diameter that decreases with each added part in the sequence, so that an intramedullary nail can be produced that is easy to insert. Particularly the shank section has at least the same or a smaller diameter than the actuator shank. The locking shank or the shank section are preferably hollow. A hollow locking shank enables a lead or an antenna to be passed through or a control unit to be accommodated. The locking shank typically comprises radial through holes for accommodating locking bolts or fragment fixing bolts for fixing the first bone fragment with respect to the locking shank. All the features described above in connection with the intramedullary nail can also be advantageously used or applied in the case of the modular system.

In embodiments of the modular system a shank section and two pairs of oppositely positioned elongated holes and additionally a shank section having only one pair of oppositely positioned elongated holes are provided. In the latter variant at least one radial opening may also be provided ensuring permanent assembly of bolts on the shank, or also no other openings.

In typical embodiments two variants of locking shanks are provided, wherein a first variant is axially straight and a second variant axially angled. The axially straight variant of the locking shank is suitable in particular for the treatment of upper leg bones (femur), whereas the variant of the locking shank with a Herzog bend is particularly suitable for treating the shin bone (tibia). In this way, a modular system is created with which several different intramedullary nails may be produced with identical components such as the actuator shank and shank section. This can reduce the production costs.

The shank section advantageously has a second axially movable inner section. The shank section also has corresponding axially aligned elongated holes through which further bolts may be passed. In this way it is possible to create an option for a distraction intramedullary nail with segment transport by using two movable inner sections and corresponding elongated holes in the shank section.

In general in this application the term "axial" is used to describe a direction along the longitudinal axis of the intramedullary nail.

BRIEF DESCRIPTION OF THE DRAWINGS

In the following, embodiments will be explained in greater detail, with reference to the accompanying drawing, in which.

DETAILED DESCRIPTION

In the following, the embodiments will be explained with reference to the figures, wherein the same reference numbers are used for identical or similar components. In some circumstances identical or similar components are not explained again in connection with every figure.

Figure 1:
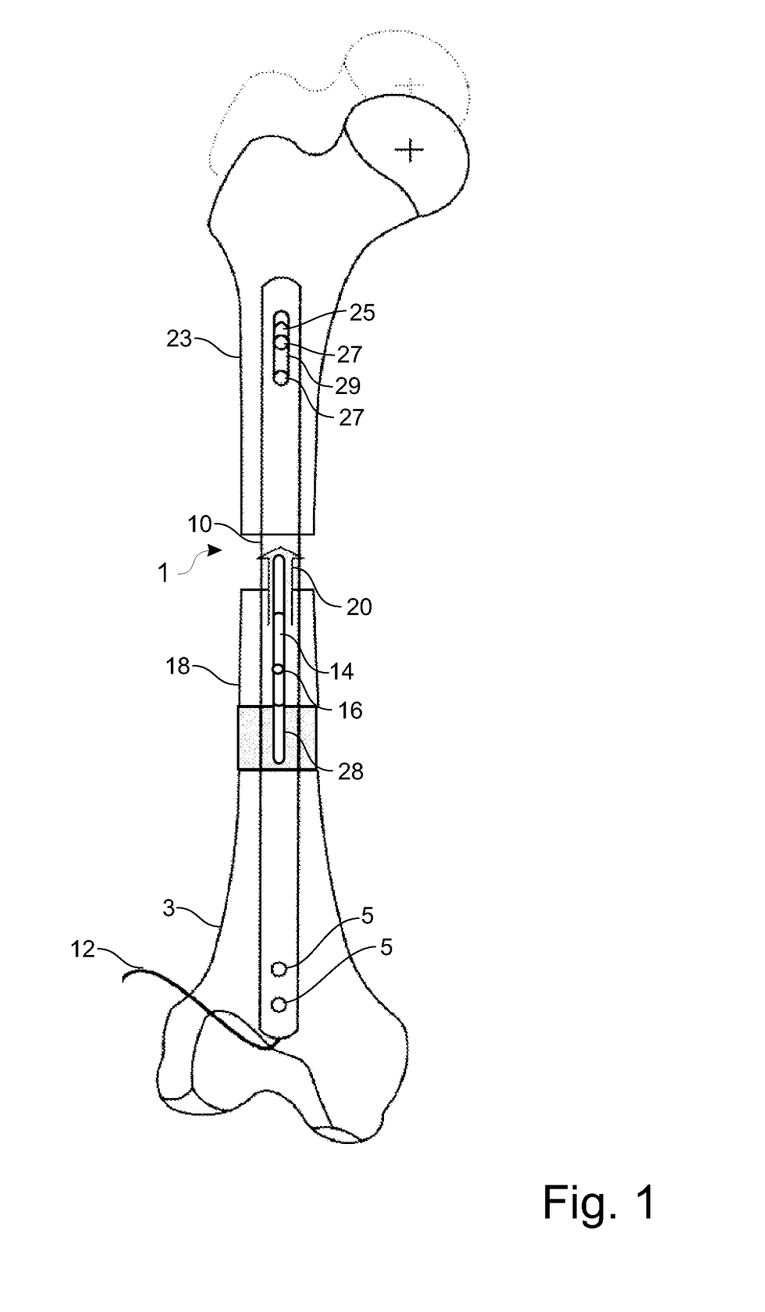
FIG. 1 is a schematic overview of an intramedullary nail with segment transport and subsequent distraction in an overview sketch.

FIG. 1 shows an intramedullary nail 1 which is locked in a first bone fragment 3. Intramedullary nail 1 is fixed in first bone fragment 3 with two locking bolts 5, which acts as locking means. Locking bolts 5 are essentially aligned parallel to the sagittal plane. Intramedullary nail 1 comprises a shank 10 in which openings for the locking bolts 5 are arranged. At the end of the intramedullary nail 1, which is locked in the first bone fragment 3, a lead 12 is provided for supplying the intramedullary nail with energy and control data.

Shank 10 of intramedullary nail 1 is partially hollow. In shank 10, at the end to which lead 12 is attached, an actuator (not shown in FIG. 1) is provided in intramedullary nail 1. The actuator serves to drive a first inner section 14. Inner section 14 has a through hole in which a segment bolt 16 is arranged. Segment bolt 16 fixes a bone segment 18 relative to first inner section 14. By operating the actuator the first inner section 14 may be pushed away from first bone fragment 3. The direction of displacement is shown by an arrow 20.

When bone segment 18 is moved, bone regrows if the speed of movement is slow enough. The regrowing bone is formed at the interface between first bone fragment 3 and bone segment 18. After having been advanced sufficiently, bone segment 18 comes into contact with second bone fragment 23. As an example, in FIG. 1 a distal fragment of a femur (upper leg bone) is shown as the first bone fragment and a proximal fragment of the femur as the second bone fragment.

Figures 5, 6:
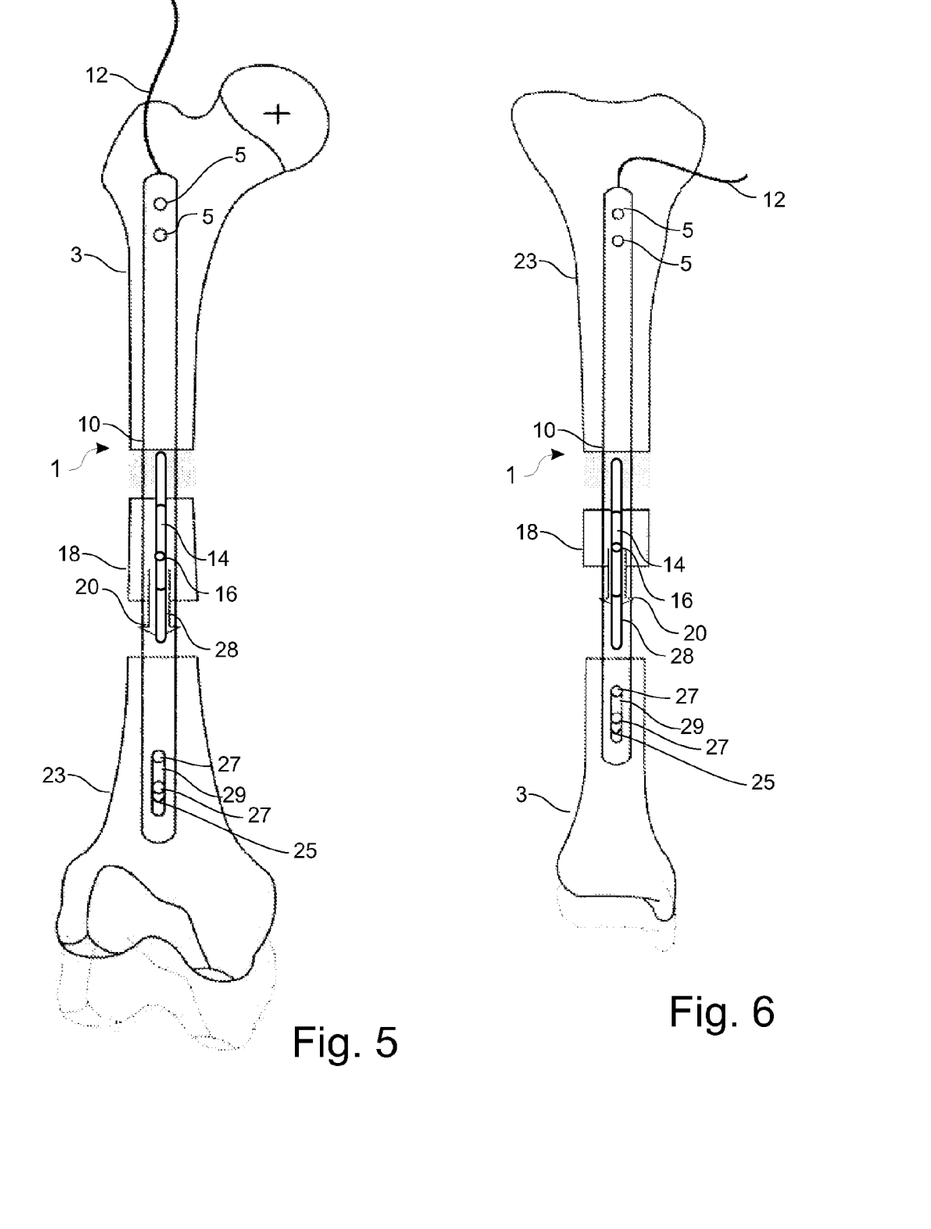
FIG. 5 shows an alternative arrangement of an intramedullary nail in a bone.
FIG. 6 shows an arrangement of an intramedullary nail in a bone other than in FIGS. 1 to 5.

Depending on the size of the bone fragments, an opposite assembly of the intramedullary nail may be advisable, see FIG. 5. In other embodiments the actuator is not arranged at the end with the lock, but at the end opposite the lock side. An actuator arranged on the end with the lock pushes against the first inner section on displacement of the first inner section, while an actuator arranged at the opposite end moves the inner section by pulling.

After bone segment 18 comes into contact with second bone fragment 23, as first inner section 14 moves farther in the direction of displacement 20, a pressure is also exerted on second bone fragment 23. In order to allow displacement of second bone fragment 23 relative to first bone fragment 3, that is to say to make distraction possible, second bone fragment 23 is arranged on a second inner section 25 which is movable relative to shank 10. Second bone fragment 23 is attached to second inner section 25 with two fragment fixing bolts 27. Fragment fixing bolts 27 are identical in design to segment bolt 16 and locking bolts 5.

Figure 2:
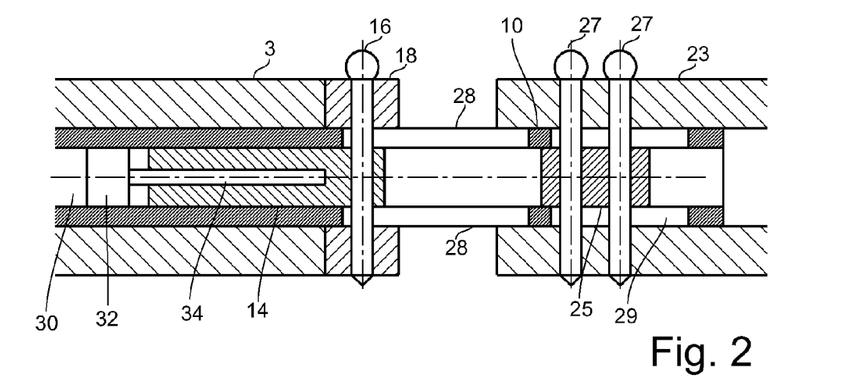
FIG. 2 is a cross-sectional view of a section of the intramedullary nail in FIG. 1 in an initial position.

All bolts used for fixing in FIGS. 1 and 2 are essentially aligned parallel to the sagittal plane. Typically, however, locking takes place perpendicularly to the sagittal plane. This offers the advantage that application of the bolt or locking means is simplified. Locking exclusively in one direction offers the advantage that the bolts may be applied more easily as they all have to be applied in the same direction.

Since in distraction second bone fragment 23 advances after the segment transport of bone segment 18 via contact between bone segment 18 and the bone fragment 23, a pressure develops between these two sections of bone which as a rule is generally great enough to support the growing together of bone segment 18 and bone fragment 23.

In the embodiment in FIG. 1, therefore, first inner section and second inner section are designed such that advance of second bone fragment 23 does not take place through contacting between inner sections 14 and 25, but due to bone segment 18 coming into contact with second bone fragment 23. This has the advantage that high pressure may be exerted on the contact surface of the two partial bone sections. However, it is also possible to allow the force to be transmitted at least partially directly from one inner section to the other inner section, for example also by means of an intermediate component arranged between the two inner sections 14 and 25 in shank 10.

In shank 10 of intramedullary nail 1, elongated holes 28 aligned in the axial direction of intramedullary nail 1 are provided for segment bolt 16 which allow segment bolt 16 to pass through them. Only one of the elongated holes 28 is shown. A further elongated hole 28 is provided on the rear. Elongated holes 29 are also provided for the fragment fixing bolts 27 at one end of shank 10 of intramedullary nail 1, wherein the end with elongated holes 29 is opposite the end with locking bolt 5. Elongated holes 28 and 29 are arranged axially one behind the other and enable guidance of the bolts.

Typical embodiments have two axially aligned elongated holes arranged opposite each other in the area of the inner section or first inner section. Other embodiments have an elongated hole on one side only. One or more additional elongated holes may be provided adjacent thereto, particularly in the area of a second inner section. The at least one further elongated hole is typically axially offset with regard to the first elongated hole, that is to say it is arranged at a different point in the axial direction of the intramedullary nail.

Also in FIG. 1, the dashed line shows the position of second bone fragment 23 after completed distraction. With embodiments of the invention, the bone may still be extended considerably after segment transport.

Figure 3:
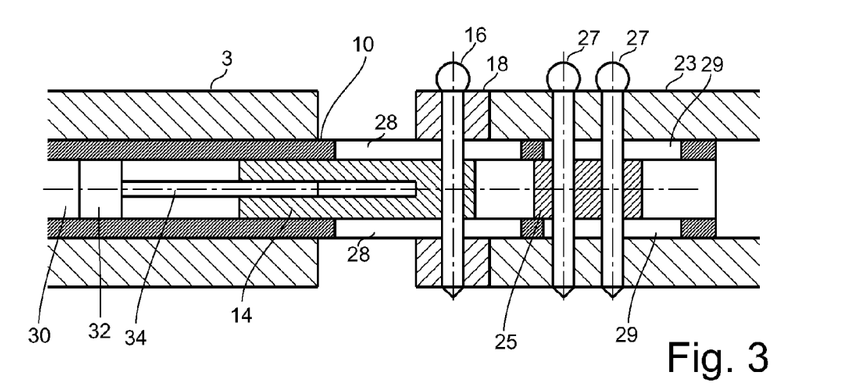
FIG. 3 shows a cross-sectional view of the intramedullary nail in FIG. 1 after completed segment transport.
Figure 4:
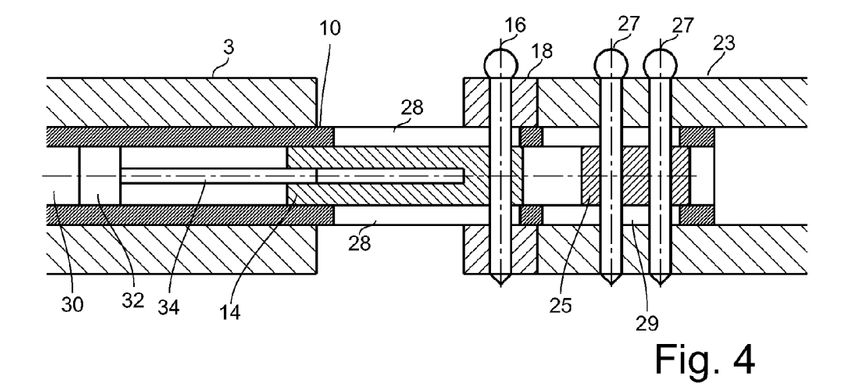
FIG. 4 shows a cross-sectional view of parts of the intramedullary nail in FIG. 1 after additional distraction.

FIGS. 2 to 4 show various states of intramedullary nail 1 in FIG. 1, wherein in FIGS. 2 to 4 only one section of the intramedullary nail and the bone are shown in a highly schematised manner. For example, the locking means for locking intramedullary nail 1 in first bone fragment 3 are not shown.

FIG. 3 also shows a partial view of an actuator motor 30. Actuator motor 30 is accommodated in multiple-component shank 10. The multiple-component structure of shank 10 will be explained in greater detail later, in connection with FIGS. 7 and 8. Motor 30 is used to drive a spindle 34 via a gear mechanism 32, which spindle engages with an inner thread of first inner section 14. With the actuator it is possible to carry out a segment transport of bone segment 18 by using spindle 34 to push first inner section 14 towards second inner section 25.

Typical embodiments comprise a motor as the actuator. Other actuators which may be used advantageously are permanent magnets driven by external magnetic fields, piezo elements, shape-memory alloys or pneumatic actuators.

The elongated holes 28 that enable segment bolt 16 (elongated holes 28) and fragment fixing bolts 27 (elongated holes 29) to pass through are also shown again in FIG. 3.

In FIG. 3 the intramedullary nail is shown in a state in which first inner section 14 is advanced so far that bone segment 18 is in contact with second bone fragment 23. If motor 30 continues to be operated and first inner section 14 is pushed farther, second bone fragment 23 will be displaced in the direction of displacement of first inner section 14. Second inner section 25 will also be moved in the direction of the end of intramedullary nail 1 by second bone fragment 23. The consequence of this is that distraction takes place after the segment transport of bone segment 18 towards second bone fragment 23. This requires a movable arrangement of shank 10 in second bone fragment 23. The length of maximum bone growth of the intramedullary nail in FIG. 3 is determined via the length of elongated hole 28, wherein the distance of the possible segment transport is determined from the length of longitudinal hole 28 less the length of longitudinal hole 29.

FIG. 4 shows the condition after completion of the distraction movement. Second inner section 25 has been moved until of the two fragment fixing bolts 27 the one at the end comes into contact with the end of elongated hole 29 of shank 10. It should be noted that in FIGS. 2 to 4 the newly grown bone between first bone fragment 3 and bone segment 18 is not shown. This is solely for the sake of clarity.

Gear mechanism 32 is a planetary gear and enables a high transmission rate. Intramedullary nail 1 also comprises a control unit which is connected to intramedullary nail 1 by means of a lead 12. The control unit enables wireless communication with the control unit from outside the body and thus also wireless control of intramedullary nail 1. Control unit may also be used to supply power to motor 30 of the intramedullary nail 1, in which case the transmission of energy to the control unit is also wireless.

FIG. 5 shows intramedullary nail 1 implanted in a femur in the opposite direction to FIG. 1. In the embodiment of FIG. 5, first bone fragment 3 is the proximal fragment of the bone and second bone fragment 23 is the distal bone fragment of the bone. Otherwise, the reader is referred to the similar description relating to FIG. 1. The configuration in FIG. 5 may be particularly advantageous if the distal bone fragment is very small.

FIG. 6 shows the implantation of an intramedullary nail 1 in a tibia. Intramedullary nail 1 is locked in the frontal plane or also the lateral plane. It is also possible to use intramedullary nails with a Herzog bend for tibias, as shown for example in FIG. 8. Inverse incorporation of the intramedullary nail in a tibia is also possible, wherein in an inverted implantation lead 12 is preferably arranged at the end of second inner section 25. This enables intramedullary nail 1 to be inserted in the tibia from the distal side thereof, and in this case the Herzog bend may be dispensed with.

Figure 7:
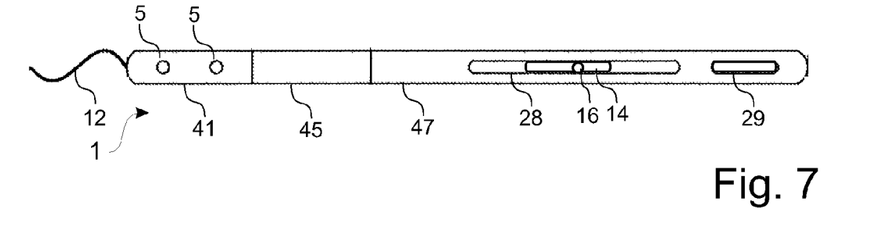
FIG. 7 shows a schematic view of an intramedullary nail assembled from a modular system.
Figure 8:
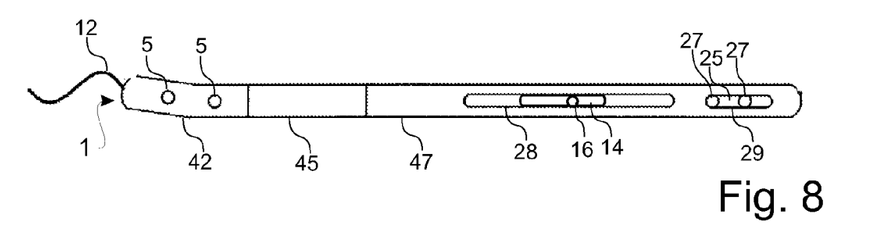
FIG. 8 shows a schematic view of a further intramedullary nail assembled from the same modular system.

FIGS. 7 and 8 show different intramedullary nails 1 that may be assembled with a modular system in accordance with embodiments.

The modular system comprises various modules, wherein two variants of locking shanks are provided for the locking module, namely a first locking shank 41 which is of straight design, and a second locking shank 42, which is axially angled. "Axially angled" means that locking shank 42 is angled a few degrees in the axial direction of intramedullary nail 1, for example between 2° and 20° or between 3° and 15°, known as a Herzog bend. Therefore, intramedullary nail 1 in FIG. 8 with the Herzog bend in locking shank 42 is particularly suitable for tibias.

An actuator shank 45 housing an actuator, or a motor, and a transmission, is welded onto each locking shank 41 and 42. A shank section 47 with axially aligned elongated holes 28 and 29 is then welded to the other end of each of the actuator shanks 45. Actuator shanks 45 and shank sections 47 are identical in the case of the intramedullary nails in FIGS. 7 and 8. For this reason, it is possible to produce a range of different intramedullary nails with a limited number of components, as a result of which production costs may be reduced. It is also possible to provide segment transport variably or to design the intramedullary nail solely as a distraction intramedullary nail. Thus, the intramedullary nail 1 in FIG. 7 comprises only one segment bolt 16, which is used, however, to fix a second bone fragment, that is to say as a fragment fixing bolt. Second inner section 25 is then no longer needed. Alternatively, a first inner section may also be used, and this then directly displaces a second inner section as a result of contact between the inner sections. Typically, all elongated holes, that is to say first elongated holes 28 and second elongated holes 29, are retained to reduce the number of components, even when the intramedullary nail is being used purely as a distraction nail. However, if a longer distraction nail is required or if the intramedullary nail has to be shorter than the distraction distance for anatomical or other reasons, elongated hole 29 may be dispensed with and the intramedullary nail shortened.

Like the intramedullary nails described with reference to FIGS. 1 to 6, the intramedullary nail 1 in FIG. 8 has a first inner section 14 together with a segment bolt 16, so that segment transport is also possible with the intramedullary nail 1 in FIG. 8. The intramedullary nail 1 in FIG. 8 also has a second inner section 25 for distraction.

In other embodiments, the second inner section may be locked. This provides the advantage that in applications in which a distraction path is not required a corresponding intramedullary nail with segment transport may be created simply by locking on the second inner section. Other embodiments of a modular system also comprise a partial shank, which only has elongated holes for accommodating a fixing means for a bone segment. In such embodiments fixing means for fixing the second bone fragment are held in radial openings of the shank section, wherein displacement of the fixing means for the second bond segment is not possible, for example due to fixed radial openings.

The modular structure of the module system enables the creation of various intramedullary nails with a limited number of components. Over and beyond the illustrated examples there are many further options for assembling intramedullary nails with the components shown. For example, it is possible to provide shorter or longer shank sections in order to produce intramedullary nails for different bone lengths with the same actuator shank. The invention is not restricted to the embodiments described above, instead but the scope of the invention is determined by the claims. More particularly, not all the illustrated components are necessarily part of the invention, this applies particularly to the human bones represented.

The invention claimed is:

1. Intramedullary nail for distraction of a long bone comprising:
   an at least partially hollow shank extending in an axial direction of the intramedullary nail;
   locking means for locking the shank in a first bone fragment of the long bone;
   a first inner section of the intramedullary nail is arranged within the shank and is movable in the axial direction and comprises a fixing means for affixing a bone segment of the long bone, wherein the shank has at least one elongated hole to enable passing through of the fixing means;
   an actuator for axially moving the first inner section; and
   a freely movable, actuator-less second inner section of the intramedullary nail arranged movably in the axial direction within the shank.

2. Intramedullary nail in accordance with claim 1, wherein the shank has a least one further elongated hole opposing the at least one elongated hole to enable passing through of at least one fragment fixing bolt for fixing a second bone fragment of the long bone.

3. Intramedullary nail in accordance with claim 2, wherein the second inner section has at least one radially orientated through hole for accommodating the at least one fragment fixing bolt.

4. Intramedullary nail in accordance with claim 1, wherein the first inner section has a radially orientated through hole for accommodating a segment bolt as the fixing means.

5. Intramedullary nail in accordance with claim 1, wherein the first and second inner sections are axially arranged one behind the other in the shank.

6. Intramedullary nail in accordance with claim 1, wherein actuator is accommodated in the shank in a fixed manner so that insertion of the intramedullary nail into the long bone is possible with the actuator accommodated.

7. Intramedullary nail in accordance with claim 1, wherein the diameter of the shank is unchanged and does not exceed 13 mm over its entire length.

8. Intramedullary nail in accordance with claim 1, wherein a Herzog bend is provided at one end of the shank.

9. Intramedullary nail in accordance with claim 1, wherein the actuator in the shank is arranged opposite the second inner section.

10. Intramedullary nail in accordance with claim 1, wherein the first inner section and the second inner section are cylindrical in shape.

11. Modular system for intramedullary nails, particularly for intramedullary nails for distraction of a long bone, comprising:
    a locking shank with locking means for locking the locking shank in a first bone fragment of the long bone;
    a hollow shank section extending in an axial direction and an inner section of the intramedullary nail is arranged so as to be movable within the shank section in the axial direction of the shank section;
    an actuator shank that comprises an actuator which is arranged in the actuator shank for axially moving the inner section, wherein the locking shank, the actuator shank and the shank section, in the form of prefabricated components, can be connected to each other in this order to form an intramedullary nail; and
    the shank section has at least one elongated hole, and also has at least one further elongated hole which is axially offset relative to the first elongated hole, wherein the shank section has two axially movable inner sections, one of which is freely movable and actuator-less.

12. Modular system in accordance with claim 11, wherein two variants of locking shanks are provided, a first variant of the locking shank is axially straight and a second variant of the locking shank is axially angled so that on the second variant an intramedullary nail with a Herzog bend can be produced.

13. Modular system in accordance with claim 11, wherein the first inner section is designed as single- or multiple component lock.

* * * * *